United States Patent
Oertel

(10) Patent No.: US 8,020,262 B2
(45) Date of Patent: Sep. 20, 2011

(54) STRIP OF MALE FASTENING MEANS, PATCH CUT THEREFROM, AND FASTENING TAPE TAB COMPRISING SUCH PATCH

(75) Inventor: Ralf G. Oertel, Neuss (DE)

(73) Assignee: 3M Innovative Properties Company, St. Paul, MN (US)

( * ) Notice: Subject to any disclaimer, the term of this patent is extended or adjusted under 35 U.S.C. 154(b) by 609 days.

(21) Appl. No.: 11/577,142

(22) PCT Filed: Dec. 2, 2005

(86) PCT No.: PCT/US2005/043568
§ 371 (c)(1),
(2), (4) Date: Apr. 12, 2007

(87) PCT Pub. No.: WO2006/062810
PCT Pub. Date: Jun. 15, 2006

(65) Prior Publication Data
US 2008/0052881 A1    Mar. 6, 2008

(30) Foreign Application Priority Data
Dec. 10, 2004   (EP) .................................. 04029356

(51) Int. Cl.
*A44B 18/00* (2006.01)
(52) U.S. Cl. .............. 24/442; 24/452; 24/446; 604/391; 428/100
(58) Field of Classification Search ............. None
See application file for complete search history.

(56) References Cited

U.S. PATENT DOCUMENTS

| 3,717,908 | A | * | 2/1973 | Perina ........................... 24/444 |
| 4,001,366 | A | | 1/1977 | Brumlik |
| 4,568,344 | A | | 2/1986 | Suzuki |
| 4,585,450 | A | | 4/1986 | Rosch et al. |
| 4,894,060 | A | | 1/1990 | Nestegard |
| 5,077,870 | A | | 1/1992 | Melbye |
| 5,318,555 | A | | 6/1994 | Sieber et al. |
| 5,605,735 | A | | 2/1997 | Zehner et al. |
| 5,607,635 | A | | 3/1997 | Melbye |
| 5,660,666 | A | | 8/1997 | Dilnik et al. |
| 5,679,302 | A | | 10/1997 | Miller |
| 5,845,375 | A | | 12/1998 | Miller |
| 5,868,987 | A | | 2/1999 | Kampfer |

(Continued)

FOREIGN PATENT DOCUMENTS
EP    0113464    7/1984

(Continued)

*Primary Examiner* — Jack W. Lavinder
(74) *Attorney, Agent, or Firm* — Kathleen B. Gross; William J. Bond

(57) ABSTRACT

The invention provides a patch of a male fastening means, in particular, a hook patch with decreased bending resistance. The patch according to the invention comprises a backing bearing a plurality of male fastening elements, in particular hook elements. The patch is integral and comprises a plurality of incisions. Said incisions do not extend across the whole width of the patch but preferably leave at least one intact bridge across the cross-direction of the patch. Furthermore, a fastening tape tab having a manufacturer's and user's end is provided, the fastening tape tab comprising a support layer bearing on its major surface of the user's end at least one fastening patch according to the invention. Furthermore, a strip is provided from which a patch according to the invention is cut.

28 Claims, 3 Drawing Sheets

U.S. PATENT DOCUMENTS

Figure 1A:
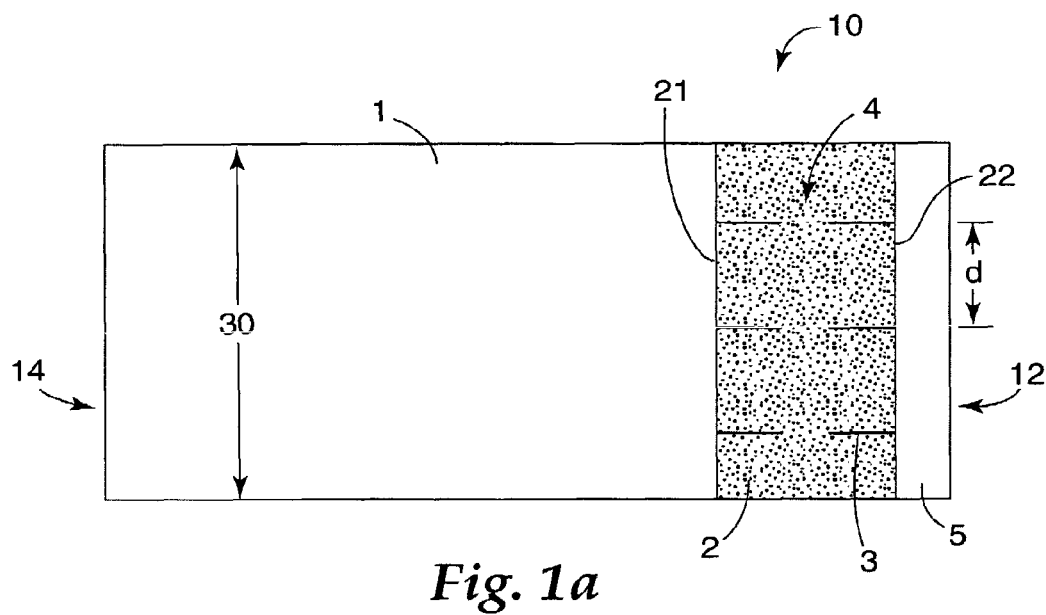

| | | | |
|---|---|---|---|
| 5,879,604 A | 3/1999 | Melbye | |
| 5,930,875 A | 8/1999 | Schreiner | |
| 5,945,131 A | 8/1999 | Harvey et al. | |
| 5,997,522 A | 12/1999 | Provost et al. | |
| 6,000,106 A | 12/1999 | Kampfer | |
| 6,030,373 A | 2/2000 | VanGompel et al. | |
| 6,039,911 A | 3/2000 | Miller | |
| 6,054,091 A | 4/2000 | Miller | |
| 6,132,660 A | 10/2000 | Kampfer | |
| 6,146,369 A | 11/2000 | Hartman | |
| 6,419,667 B1 | 7/2002 | Avalon et al. | |
| 6,463,633 B1 | 10/2002 | Sangani et al. | |
| 6,544,245 B2 | 4/2003 | Neeb et al. | |
| 6,558,602 B1 | 5/2003 | Melbye | |
| 6,575,953 B2 | 6/2003 | Olson | |
| 6,588,073 B1 * | 7/2003 | Zoromski et al. | 24/446 |
| 6,635,212 B1 | 10/2003 | Melbye | |
| 6,994,698 B2 | 2/2006 | Leak et al. | |
| 7,032,278 B2 | 4/2006 | Kurtz, Jr. | |
| 7,048,818 B2 | 5/2006 | Krantz et al. | |
| 7,125,400 B2 | 10/2006 | Igaue et al. | |
| 7,223,314 B2 | 5/2007 | Provost | |
| 7,241,483 B2 | 7/2007 | Ausen et al. | |
| 7,361,246 B2 | 4/2008 | Chang et al. | |
| 7,371,302 B2 | 5/2008 | Miyamoto et al. | |
| 7,373,698 B2 | 5/2008 | Erdman et al. | |
| 7,407,496 B2 | 8/2008 | Petersen | |
| 7,444,722 B2 * | 11/2008 | McDaniel et al. | 24/446 |
| 7,578,813 B2 | 8/2009 | Mitsui et al. | |
| 7,670,522 B2 | 3/2010 | Ausen et al. | |
| 2002/0016581 A1 | 2/2002 | Kline | |
| 2003/0008106 A1 | 1/2003 | Guenther | |
| 2003/0130644 A1 | 7/2003 | Baker | |
| 2003/0145440 A1 | 8/2003 | Ausen | |
| 2003/0182776 A1 | 10/2003 | Ausen | |
| 2004/0068848 A1 | 4/2004 | Ausen | |
| 2004/0111844 A1 | 6/2004 | Ausen | |
| 2004/0121694 A1 | 6/2004 | Shepard et al. | |
| 2004/0147890 A1 | 7/2004 | Nakahata et al. | |
| 2004/0261232 A1 | 12/2004 | Kurtz, Jr. et al. | |
| 2004/0261233 A1 | 12/2004 | Kingsford et al. | |
| 2007/0035060 A1 | 2/2007 | Harvey et al. | |

FOREIGN PATENT DOCUMENTS

| | | |
|---|---|---|
| EP | 0755665 | 1/1997 |
| EP | 1 066 008 B1 | 3/2004 |
| JP | 61-179308 | 8/1986 |
| WO | WO 94/02091 | 2/1994 |
| WO | 96/10481 | 4/1996 |
| WO | WO 96/19174 | 6/1996 |

\* cited by examiner

STRIP OF MALE FASTENING MEANS, PATCH CUT THEREFROM, AND FASTENING TAPE TAB COMPRISING SUCH PATCH

CROSS REFERENCE TO RELATED APPLICATIONS

This application is a national stage filing under 35 U.S.C. 371 of PCT/US2005/043568 filed Dec. 2, 2005, which claims priority to EP 04029356.5; filed Dec. 10, 2004, the disclosure of which is incorporated by reference in its/their entirety herein.

The present invention relates to a strip of a male fastening means, in particular a hook strip having a high flexibility, and a patch cut therefrom, said patch being for use in a fastening laminate, in particular a fastening tape tab. Such fastening tape tabs may be particularly used in diapers or feminine hygiene articles as mechanical closure component.

Known fastening tape tabs used in, for example, disposable diapers usually comprise a support layer bearing on one of its major surfaces a patch of fastening means in order to securely join parts of the diaper together. Said tab of fastening means may for example comprise a hook patch which usually extends across the whole width of the fastening tape tab. Therefore, the whole width and length of the hook patch is adding to the bending performance of the fastening tape tab. Since the hook patch is comprised of a rather rigid material, this may cause the problem that the fastening tape tab may not be flexible enough to conform to a movement of the wearer and thus may decrease the comfort of wearing. This is even more critical if the width of the fastening tape tab is large as in the case of recently more common elasticized fastening tape tabs, in particular in so-called big-ear applications, like pull-up diapers or training pants.

U.S. Pat. No. 6,146,369 describes an extensible tab fastener for a disposable diaper comprising a laminate of an extensible facestock and an ordinarily nonextensible mechanical fastener. The nonextensible mechanical fastener is rendered extensible by providing in at least the nonextensible portions thereof a plurality of separation interfaces or parting planes extending through the thickness of the nonextensible portion or portions at spaced locations in the direction of desired extensibility.

EP-A-0 755 665 describes a disposable undergarment having a tape fastener for releasably joining front and rear regions of the undergarment. The tape fastener comprises a soft base panel member and at least two relatively rigid fastening panel members bonded to an inner surface of the base panel member in order to eliminate the problem that the whole of the tape fastener might be unintentionally disengaged at once.

U.S. Pat. No. 6,575,953 describes a disposable absorbent article having an absorbent chassis and a fastening system that aims at providing beneficial fit attributes yet affording easier access to the interior of the article for purposes of inspection. The fasteners of the absorbent article include discrete hook patches forming a fastening component comprising hinge areas.

EP-B-0 113 464 discloses a waist band provided on a diaper comprising an intermediate area, an adhesive area and a finger lift portion. Slits are applied in the cross-direction in either the intermediate section, the adhesive section or in both to allow these sections to function independently from each other.

In US-A-2002/0016581 a fastening system having a hook fastening element is disclosed. The fastening element comprises an attached portion, partly joined to the article, at least one liftable portion extending from the attached portion, and at least one hinge line disposed in an angle of less than 90° relative to the primary direction of the load bearing. The hinge line is positioned between and thus separates the attached portion and the liftable portion.

In WO96/19174 a fastening tab is described, said fastening tab including a manufacturer's bond end and a user's end, wherein said user's end includes a mechanical fastener component and is configured to have a disengagement ratio of at least 1.5:1. The user's end may be multi-lobed or may define sheer channels in the mechanical fastener component.

There is a need to provide a strip of male fastening means a patch of male fastening means to be cut from said strip, in particular a patch of hook strip, with improved bending performance. The fastening patch should advantageously be more flexible than prior cut patches yet still properly handleable. There is also a need to provide a fastening tape tab comprising such a fastening patch. When used, e.g., as fastening means for a baby or adult diaper or in feminine hygiene articles, in particular in so-called big-ear applications, the fastening tape tab should be able to conform to the body shape and the movements of the wearer in order to increase the comfort of the wearer and decrease the risk of red marks on the wearer's skin. More generally, the fastening tape tab should conform better to any surface to which it is attached.

According to the present invention, a patch of a male fastening means with improved flexibility and decreased bending resistance is provided as well as a strip from which such a patch can be cut. The patch according to the invention comprises a backing bearing a plurality of male fastening elements, in particular hook elements. The patch is preferably cut from an elongate strip of a male fastening means, e.g., a hook strip, and has two longitudinal edges along its length, i.e., two edge lines which both substantially extend in the machine direction of the strip from which the patch has been cut. The cross-direction is defined as the direction perpendicular to the machine direction in the plane of the flat patch. The term hook describes all types of hooks suitable to form a hook-and-loop fastener together with a corresponding landing zone. The hook may have all kind of shapes, including mushroom type hooks. The patch is integral and comprises at least one incision. The term "integral" as used above and below means that the patch forms one piece, i.e. the incisions are non-throughgoing. Here, the term incision describes both, an incision wherein no material is removed from the substrate, e.g., the strip, in which the incision is made, like incisions made with a knife or a pair of scissors, but also an incision wherein material is removed from the substrate to be cut, e.g., when the latter type of incision is punched into the substrate. In the following, the latter incision will be called an insection.

Said at least one incision does not extend across the whole width of the patch but leaves at least one intact land of material across the cross-direction of the patch. Thus, a portion of the patch in machine direction is uncut. The incisions may extend through one or both edge lines of the patch. Preferably, the at least one incision substantially extends in the cross-direction of the patch. However, the incisions can also extend in a direction between the cross-direction and the machine direction. The incisions extending through one of the edge lines of the patch may be aligned with the incisions extending through the other edge line, i.e., extend in cross-direction pointing towards the same spot in the center of the patch, but may also be staggered in machine direction along the two edge lines. The incisions extending through the two edge lines, respectively, can have the same or a different length from the respective edge line towards the center of the patch. The option of differing incision lengths exists also when the incisions from the one side and the other side are not pointing towards the same spot but are staggered, i.e., shifted in the machine direction of the fastening patch. Moreover, the incisions may also extend at an angle between the machine direction and the cross-direction.

The lands of uncut material preferably provide a bridge of intact material extending in the longitudinal direction (machine direction) of the strip. The width of the remaining narrow bridge with intact material should be selected so as to increase flexibility but should provide sufficient strength to the strip before its cutting into patches to allow processing and converting of the strip. The width of the remaining bridge preferably is less than about 10 mm, more preferably less than about 5 mm and more preferably less than about 3 mm, but the width is in any case above 0 mm, and preferably at least 1 mm. In case incisions are cut through both edge lines of the strip the remaining lands may not be aligned in the longitudinal direction of the strip. The remaining lands may then form a bridge which is curved, i.e., a continuous but curved path of intact material extending generally in the longitudinal direction of the strip.

The distance between incisions on the same edge line in machine direction can be less than about 70 mm, more preferably less than about 15 mm and even more preferably less than about 7 mm. Preferably, the distance is at least 2 mm, more preferably at least 4 mm or even more preferably at least 5 mm.

The incisions can also be designed in such a way that two or more intact narrow bridges are provided across the cross-direction of the patch. This may be preferred when using wide strips and large patches.

The incisions according to the present invention may be cut in the strip, for example by using rotary knives, laser cutting, perforating, or other techniques. Such incisions may have any shape and can be, for example, triangular, rectangular, oblong, curved, T-shaped or can also have an irregular shape.

The longitudinal edges of the elongate strip from which the patch is cut need not be straight linear edge lines that are parallel to each other. Also edge lines that are irregular or have a regular pattern, like a wavy edge line, can be used for this purpose. Strips with a wavy edge line on each side of the strip can preferably be cut out of a stock roll with minimized inherent waste in that at least two strips are cut out of the stock roll adjacent to each other in such a way that a wavy edge line of one strip corresponds to a wavy edge line of the other strip, i.e., in a nested configuration. Such strips can be used for various applications. Additional incisions into a wavy edge strip will further increase flexibility of the strip. Irrespective of the amplitude and the frequency of the wave in the edge, the still intact center of the strip material forming a bridge will deliver the required strength in machine direction, and a strip having high amplitude and frequency wavy edges will act similarly to a strip where narrow pieces of material are punched out along its edge lines. Instead of a wavy cut edge line also other suitable edge contours may be provided which act in the same or similar way, such as a strip edge with triangular, saw-tooth like, rectangular or generally curved characteristics.

The incisions according to the present invention may also be provided in the form of insections in the fastening strip and the patch. Such insections can be obtained by punching out of the strip or the patch, for example, by die-cutting a narrow piece of material. The insection may have a triangular, rectangular, oblong, sinusoidal, generally curved or any other shape which is suitable to increase the bending performance of the fastening strip and patch.

The invention further provides a fastening tape tab having a manufacturer's end and a user's end. The fastening tape tab of the invention comprises a support layer bearing on one of its major surfaces in the area of the user's end at least one fastening patch according to the invention. The patch has a proximal end facing the manufacturer's end of the tape tab and a distal end facing the user's end of the tape tab. The support layer of the fastening tape tab may be continuous at least at the location of the incisions in the fastening patch. The incisions may also extend through both, the support layer and the patch, in particular in case at least one of the incisions extends through the edge line on the proximal end of the patch and at least one of the incisions extends through the edge line on the distal end of the patch.

Further, a strip of a male fastening means from which fastening patches can be cut, and methods of manufacturing such a strip and patch of the invention as well as a method of manufacturing a fastening tape tab are provided.

Hook strips that can be used as starting material in the present invention are known to a person skilled in the art. Hook strips to be used in the present invention are described, for example, in U.S. Pat. No. 4,894,060, US-A-2004/0111844, US-A-2003/0145440, US-A-2003/0182776 and US-A-2004/0068848. General background information on hook webs including stem webs without hook heads can be found, for example, in U.S. Pat. No. 5,077,870, U.S. Pat. No. 5,607,635, U.S. Pat. No. 5,679,302, U.S. Pat. No. 6,132,660, U.S. Pat. No. 6,054,091, U.S. Pat. No. 6,039,911, U.S. Pat. No. 6,000,106, U.S. Pat. No. 5,879,604, U.S. Pat. No. 5,868,987, U.S. Pat. No. 58,453,785 U.S. Pat. No. 5,845,375, U.S. Pat. No. 6,635,212, U.S. Pat. No. 6,558,602. Hook strips which may be used as a starting material in the present invention are commercially available, e.g., under the tradenames CS-600 or CS-1010 available from 3M Company, St. Paul, USA.

The fastening tape tabs of the invention may be used on baby or adult diapers or feminine hygiene articles. The invention is however not limited to personal care articles but may also be used in other industrial applications where it is important that the fastening patch or fastening tape tab easily follows the movement of the article to which the hook patch is attached. Such applications may be for example in the upholstery, car and air plane industry or in other textile applications.

The fastening patch of the present invention provides the specific advantage that due to the incisions the rigidity of the patch is decreased which causes a higher flexibility of the fastening tape tab to which the patch is provided. Since the strip from which the patch may be cut, and patch are integral, sufficient strength in machine direction for converting is provided. Since the bending force is decreased with the incised fastening patches, the fastening tape tabs are conforming better to the shape or to movements of the articles to which the patch is attached, e.g., to the movements of the user of a diaper. Therefore, the comfort of wearing is increased and the risk of red marks on the wearer's skin is reduced. As the bending is easier, also the risk of disengagement of the hooks of the patch from its engagement surface, e.g., from a loop surface, is decreased as the hook and loop components can move more synchronously. The advantage is significantly increased the larger the width of the fastening tape tab and thus the width of the patch is. Furthermore, the patch of the present invention may also provide increased flexibility in the plane of the patch due to its lower resistance against bending in said plane.

In the following, the invention is described in more detail with reference to the Figures.

Figure 1B:
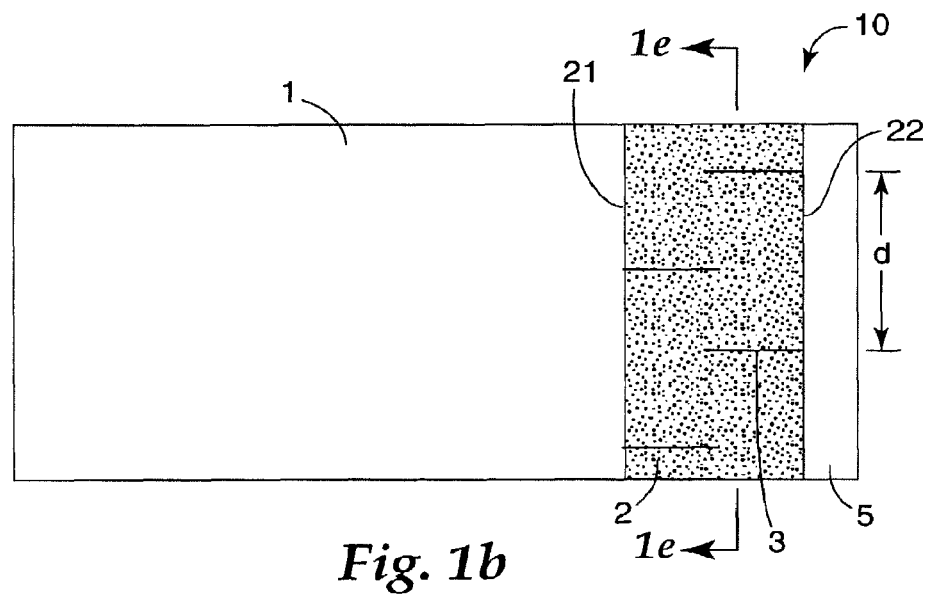
Figure 1C:
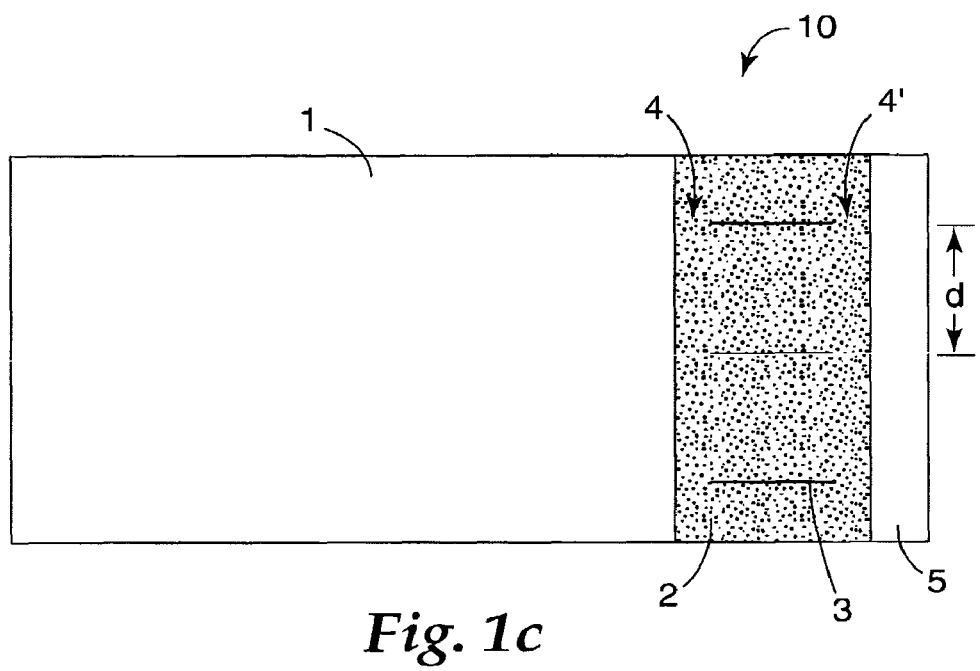
Figure 1D:
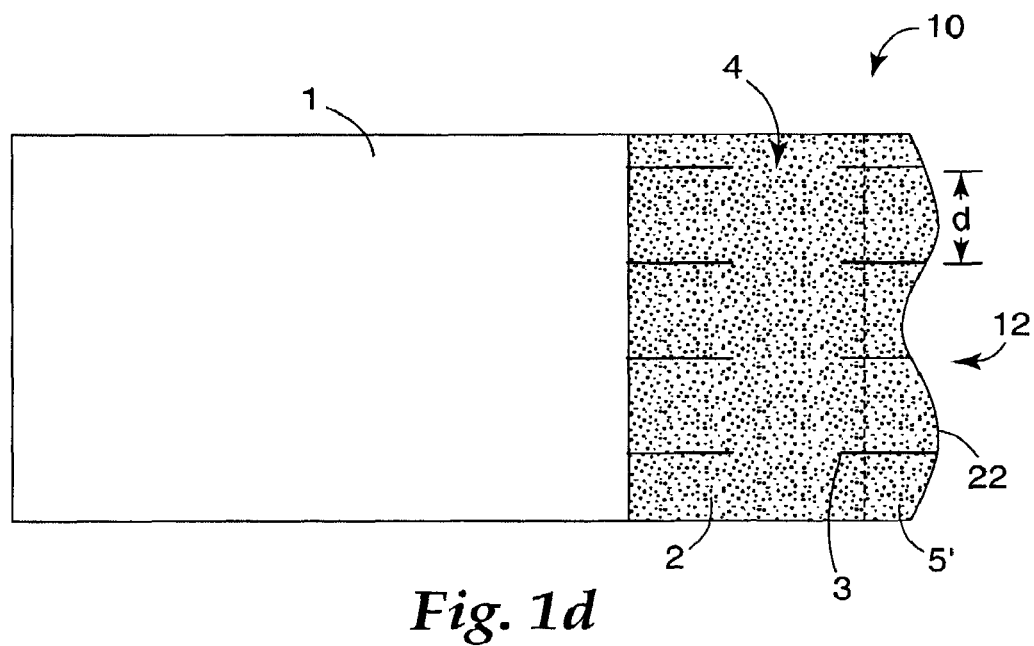
Figure 1E:
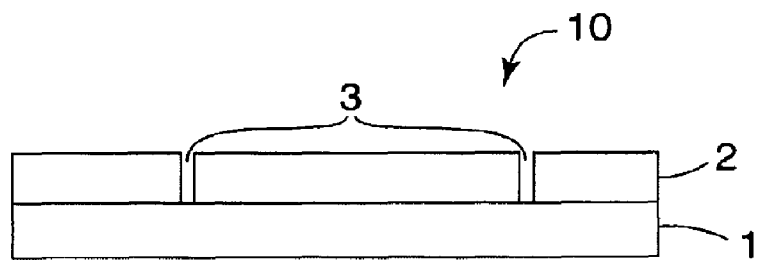
Figure 2:
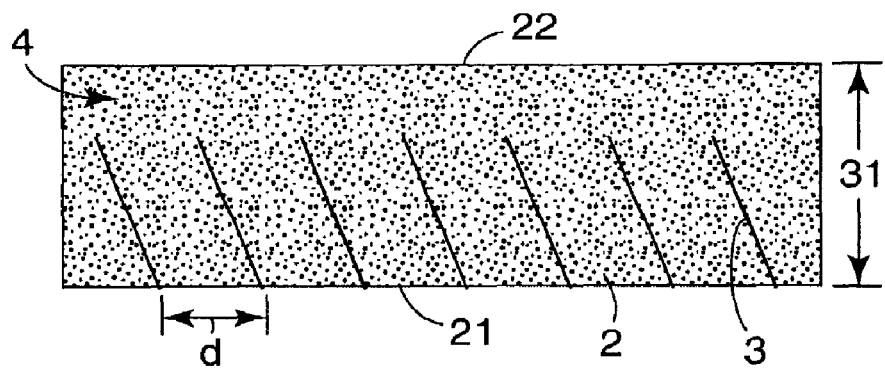
Figure 3:
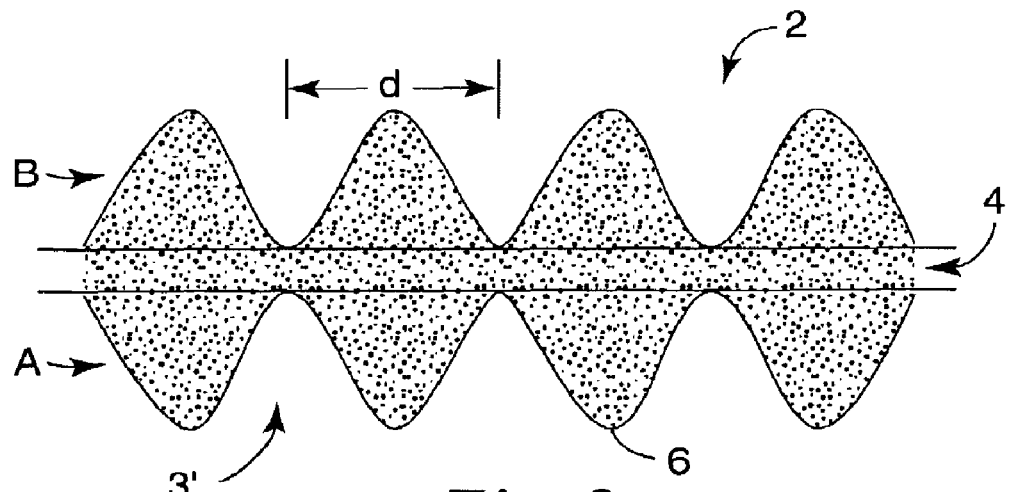

FIG. 1(a) to (e) schematically show fastening tape tabs according to the present invention with preferred arrangements of the incisions provided on the patch according to the present invention, FIG. 2 shows a further arrangement of the incisions according to the invention, and FIG. 3 shows an embodiment of the patch according to the invention comprising incisions in the form of insections.

FIG. 1(a) shows a fastening tape tab 10 for use, for example, in a diaper in accordance with an embodiment of the present invention. The fastening tape tab 10 has a manufacturer's end 11 and a user's end 12. The fastening tape tab 10 comprises a substrate or support layer 1 and at least one precut patch 2 of a male fastening means, preferably hook means, according to the invention. The precut patch 2 is arranged on a major surface of the user's end 12 of the support layer. The patch 2 has a proximal end facing the manufacturer's end 11 of the tape tab 10 and a distal end facing the user's end 12 of the tape tab 10. The edge line 21 is situated on the proximal end of the patch 2, the edge line 22 is situated on the distal end of the patch 2. The fastening tape tab 10 has a width 30 and further comprises a finger lift portion 5.

The precut patch 2 preferably is cut from a hook strip and comprises at least one incision 3. The support layer 1 is preferably comprised of a nonwoven or woven textile web or a thin flexible polyolefin backing. The incised or precut fastening patch 2 of the invention may be attached to the support layer 1 by using an adhesive, ultrasonic welding, thermocalandering, stitching or other suitable techniques.

In FIG. 1(a), a preferred embodiment of the precut hook strip according to the present invention is schematically shown. The hook strip 2 shown in FIG. 1(a) comprises six incisions 3 which extend through both edge lines 21, 22 in cross-direction of the patch 2. The three incisions 3 extending from both edge lines, respectively, are aligned and have the same length. However, the incisions on the two edge lines may also have different lengths. The incisions 3 extending from both edge lines, respectively, leave an intact bridge 4 which is centered in the cross-direction of the patch 2. In case the incisions have different lengths on both edge lines, the bridge will not be centered. The intact bridge 4 has a width of less than 10 mm, preferably less than 5 mm and more preferably less than 3 mm. However, the width of the bridge 4 is in any case above 0 mm and should preferably be at least 1 mm in order to allow processing of the patch and the strip from which it is cut. The distance d between subsequent incisions 3 in machine direction can be less than 70 mm, preferably less than 15 mm and more preferably less than 7 mm, and is preferably at least 2 mm, or at least 4 mm. The distances d between subsequent incisions 3 may be equal, as shown in FIG. 1, or may be different.

FIG. 1(e) schematically shows a cross-sectional view of the fastening tape tab 10 of FIG. 1(a) along the line A-A indicated in FIG. 1(a). The incisions 3 extend through the hook patch 2 but not through the support layer 1. The incisions 3 which were obtained by cutting without removing material are shown out of scale in FIG. 1(e) to make them better recognizable.

In FIG. 1(b) a further embodiment of the arrangement of the incisions 3 is shown. In this embodiment, the incisions 3 arranged on both edge lines of the patch 2 are not aligned with respect to each other but are in a staggered arrangement. In the embodiment shown in FIG. 1(b) there is no intact straight bridge left in the machine direction of the patch but an intact curved bridge exists which forms a continuous path on the strip. The necessary stability for processing is maintained due to the staggered arrangement of the incisions 3.

In the embodiment shown in FIG. 1(c) the incisions 3 do not extend through one of the edge lines of the patch 2 but are centered on the patch 2 leaving two intact bridges 4 and 4' along both edge lines of the patch 2.

The embodiment shown in FIG. 1(d) shows a fastening tape tab 10 comprising a patch 2 according to the invention which has a non-straight edge line 22 on the distal end of the patch. The incisions 3 are aligned as shown in FIG. 1(a). In the embodiment shown in FIG. 1(d) no fingerlift area is provided on the user's end 12 of the fastening tape tab but the patch 2 extends to the user's end 12 of the fastening tape tab. In order to allow the user to lift the fastening tape tab, an area void of hooks or of crushed hooks is provided on the outer portion 5' of the patch 2 in order to allow gripping of the user's end 12 without discomfort.

In FIG. 2, an alternative arrangement of incisions 3 on the patch 2 of the invention is shown. In this embodiment, the incisions 3 only extend from one edge line 21 of the patch 2 which has a width 31. The incisions 3 do not extend perpendicular to the edge line 21 of the patch 2 but are inclined in a certain angle with respect to the cross-direction of the patch 2. The angle may be in the range of 10 degrees to 80 degrees, preferably 30 degrees to 60 degrees, and most preferably about 45 degrees. In this embodiment the intact bridge 4 is arranged along the edge line 22 which is situated opposite the edge line 21 through which the incisions 3 extend.

In FIG. 3, an alternative embodiment of the present invention is shown. According to this alternative embodiment the incisions 3' provided in the patch 2 of the present invention are formed as insections formed in either one or both edge lines of the patch 2. Such insection can be formed by punching out material from the strip. Another possibility to form insections is to stretch an incised strip in machine direction so that insections are formed at positions where the strip is incised.

In this embodiment, hook strips are used which are cut out with a wavy edge knife in a way that at least one edge line, or both edge lines have a wavy edge pattern, for example a sinusoidal edge pattern. Both sides of the hook strip may have a different wavy edge geometry, e.g. different frequencies of a sinus-curve. The cutting may be carried out without waste as the complimentary hook strip next to the one which is shown is also a functional one with the complimentary wavy edge. In this case no material will be removed. The wavy edge is shaped in a way that a narrow center part of the hook strip is still intact, leaving a bridge 4. Thus the total hook area offered is extremely large compared to the narrow center part which will primarily contribute to the bending force.

The shape of the wavy edge can be mathematically altered in a lot of ways, e.g., in frequency and amplitude, but also the shape of the curve may be different, e.g., rectangular. When having a rectangular shape, the amplitude would determine how deep the insection is and the frequency would determine how often an insection occurs, or the distance between insections.

FIG. 3 shows a hook strip left intact in the center with large wavy edge hook wings 6 on both sides. The intact bridge 4 provides sufficient strength to the patch.

For the hook patch shown in FIG. 3, the bending force is decreased compared to a patch having straight edges with the same size. In the example shown in FIG. 3, the ratio of the area of the intact bridge 4 to the total area of the patch 2 is only about 23%. That means that only 23% of the area of the patch 2 contribute to the bending of the patch 2, whereas the total area of the patch 2 contributes to the fastening performance of the patch 2, since the whole area of the patch 2 comprises fastening means which can engage with complementary fastening means, e.g., a loop surface forming the counterpart of the fastening patch of the invention to which it can be attached. That means that 77% of total area lies outside of the intact bridge 4 which mainly will contribute to the bending properties of the fastening tab. In the case of a patch having straight edges and no incisions, the above ratio is 100% which means that all of the area which contributes to the fastening performance also contributes to the bending of the patch. Preferably the ratio of the area of the intact bridge to the total area of the patch is less than 50%, preferably less than 40%, more preferably less than 30% or even less than 20%.

The sinusoidal wave can be further altered becoming a rectangular geometry. In a further embodiment of the invention the incisions can be provided in the form of triangular insections provided on one or both sides of the hook strip.

The patch according to the present invention can be used on a baby or adult diaper as hook closure component. To this patch forces from the user of the diaper are applied when it is moved with a vector which is pointing into a direction perpendicular to the plane of the unbended diaper, causing bending of the patch. Such forces may be caused by the movement of a user, in particular a body when wearing the diaper. The bending force is decreased with the incised patches according to the invention. The fastening tape tabs thus are better conformable to the movements of the user of the diaper which increases the comfort of wearing and provides less red marks. As the bending is easier also the risk of hook disengagement from the loop surface of the diaper is decreased as the hook and loop components can move more synchronously. These advantages significantly increase the larger the fastening tab and thus the patch width is. Precut hook patches of the invention can also be used on a wide, large elastic or non-elastic diaper ear used, e.g., in pull-up diapers or convertibles.

The incised fastening patch of the invention can be used in feminine articles as well. In the patent literature various hook closure systems are described which are used as attachment system. These very large hook strips contribute to the flexural rigidity of pantiliners. However, in this sensible application a high flexibility of the finished article is important. Incised hook patches allow higher flexibility of the pantiliner in the direction perpendicular to its plane when not bend so that the pantiliner is conforming to the body shape in a better way.

Further, the invention is not limited to personal care articles like diapers or feminine hygiene articles, but may be used in other industrial applications where it is important that the hook patch or fastener tape tab follows the movement of the article to which the hook patch is attached. Applications can be for example in the upholstery, in cars, particularly for the roofliner of cars, the air plane industry or in other textile applications.

In particular if the incisions extend from one side edge only, with intact material directly at the opposite edge, an incised strip of male fastening means of the present invention is able to be bent easily without folds and wrinkles in the plane of the strip towards the side of the intact material. Upon bending the incisions 3 or insections 3' are widened, in particular, at the side edge from which such incisions or insections extend. For example it was found that with an adhesive coated incised hook strip it is possible to adhere the hook strip to an article such that the hook strip was bowing to one side without having folds and wrinkles. This tendency for curved applications would particularly be an advantage where longer hooks strips are used in applications in non-hygiene markets.

In the following, examples of hook patches and strips are described. The exemplary hook strips were produced using standard commercial products available from 3M Company, St. Paul, USA. In particular, hook strips with the trade names CS-600 having a width of 15 mm (Hook 1) and CS-1010 having a width of 25 mm (Hook 2) were used. The CS-600 hook has a basis weight of 108 g/m$^2$, a hook density of 248 hooks/cm$^2$, the caliper of the backing is 109 µm, and the total caliper of the hook web is 390 µm. The CS-1010 hook has a basis weight of 162 g/m$^2$, a hook density of 81 hooks/cm$^2$, the caliper of the backing is 173 µm, and the total caliper of the hook web is 658 µm. Furthermore, a Binder hook (Hook 3) has been used which is commercially available from Gottlieb Binder Gmbh & Co., Holzgerlingen, Germany. The Binder hook has a basis weight of 194 g/m$^2$, a hook density of 294 hooks/cm$^2$, the caliper of the backing is 187 µm, and the total caliper of the hook web is 463 µm. The hook density and the calipers were measured using a microscope which is available from Mitotoyo Corporation, Japan under the trade name TM-500 Measuring Microscope.

The bending length as an indication of flexibility was measured according to test method ERT 50.5-99 recommended by EDANA; EDANA is the abbreviation for "European Disposables And Nonwovens Association" which is located in Brussels, Belgium. In this test method, a rectangular strip of fabric is supported on a horizontal platform with the long axis of the strip parallel to the long axis of the platform. The strip is advanced in the direction of its length so that an increasing part overhangs and bends down under its own weight. When the leading edge of the test piece has reached a plane passing through the edge of the platform and inclined at an angle of 41.5° below the horizontal, the overhanging length will equal twice the bending length of the test piece, end thus the bending length can be calculated.

The results of this test for non-adhesive coated hook strips as described above, which were cut such that incisions were located in machine direction at a distance of 5 mm with an intact, centered bridge of 5 mm width, are shown in Table 1.
Table 1:

TABLE 1

|  | Overhanging length in mm of non-incised hook strip | Overhanging length in mm with incised hook strip | Reduction of bending length in % by incision |
|---|---|---|---|
| Hook 1 | 76.3 | 53.9 | 29.4 |
| Hook 2 | 161.2 | 99.0 | 38.6 |
| Hook 3 | 158.5 | 124.4 | 21.5 |

The results of this test for non-adhesive coated hook strips, which were cut such that incisions were located in machine direction at a distance of 10 mm with an intact, centered bridge of 3 mm width, are shown in Table 2.
Table 2:

TABLE 2

|  | Overhanging length in mm of non-incised hook strip | Overhanging length in mm with incised hook strip | Reduction of bending length in % by incision |
|---|---|---|---|
| Hook 1 | 76.7 | 62.1 | 19.0 |
| Hook 2 | 157.5 | 108.0 | 31.4 |

As can clearly be seen from Tables 1 and 2, the bending length is significantly decreased when the tested strips are incised in accordance with the invention.

Although the invention has been described and illustrated with reference to specific illustrative embodiments thereof, it is not intended that the invention be limited to those illustrative embodiments. Those skilled in the art will recognize that variations and modifications can be made without departing from the scope of the invention as defined by the claims.

The invention claimed is:

1. An elongate strip of a male fastening means the strip having two longitudinal edges along its length and having a width and a thickness, said strip comprising a backing bearing a plurality of male fastening elements projecting from the backing surface, wherein the backing is not attached to a support layer, and wherein said strip has a plurality of incisions cut through the entire thickness of the strip along a portion of the strip so as to leave an intact bridge of the backing in a cross-direction of the strip, which incisions do not remove material from the strip and increase the flexibility of the strip while leaving the strip intact.

2. The strip according to claim 1, wherein the strip has a substantially constant width in its cross-direction between its longitudinal edges.

3. The strip according to claim 1, wherein at least some of said incisions extend through one longitudinal edge of the strip.

4. The strip according to claim 3, wherein at least some of said incisions extend through the other longitudinal edge of the strip.

5. The strip according to claim 4 wherein the incisions extending through opposite longitudinal edges of the strip and are aligned.

6. The strip according to claim 4 wherein the incisions extending through opposite longitudinal edges of the strip and are staggered.

7. The strip according to claim 5 wherein said bridge is of substantially constant width.

8. The strip according to claim 7 wherein said incisions on at least one edge are all equal length.

9. The strip according to claim 6 wherein said bridge is of substantially constant width.

10. The strip according to claim 9 wherein said incisions on at least one edge are all equal length.

11. The strip according to claim 1, wherein at least some of said incisions are arranged such that they do not extend through any of the two longitudinal edges.

12. The strip according to claim 1, wherein at least some of said incisions extend substantially in a cross-direction of the strip.

13. The strip according to claim 1, wherein at least some of said incisions extend in a direction inclined to a cross-direction of the strip.

14. The strip according to claim 1, wherein said bridge is centrally arranged in the cross-direction of the strip.

15. The strip according to claim 1, wherein said bridge extends along one or both longitudinal edges of the strip.

16. The strip according to claim 1, wherein said at least one bridge is less than about 10 mm wide.

17. The strip according to claim 1, wherein the distance (d) between adjacent incisions in the length direction of the strip is less than about 70 mm.

18. The strip according to claim 1, wherein said male fastening means are hooks.

19. The strip according to claim 1 wherein the distance between adjacent incisions in the length direction of the strip is less than 15 mm.

20. The strip according to claim 1 wherein the distance between adjacent incisions in the length direction of the strip is less than 7 mm.

21. An integral patch of a male fastening means, wherein the patch has two longitudinal edges along its length and having a width and a thickness, said patch comprising a backing bearing a plurality of male fastening elements projecting from the backing surface, wherein the backing is not attached to a support layer, and wherein said patch and has a plurality of incisions cut through the entire thickness of the patch along a portion of the patch so as to leave an intact bridge of the backing in a cross direction of the patch, which incisions do not remove material from the strip and increase the flexibility of the patch while leaving the patch intact.

22. A fastening tape tab having a manufacturer's end and a user's end, said fastening tape tab comprising a support layer and at least one patch on one of its major surfaces in the area of the user's end, said patch comprising a backing bearing a plurality of male fastening elements and having a plurality of incisions cut through the entire thickness of the patch so as to increase the flexibility of the patch while keeping it in a single piece, wherein the incisions do not remove material from the patch, wherein said patch has a proximal end facing the manufacturer's end of the tape tab and a distal end facing the user's end of the tape tab, and wherein at least one incision in the patch extends through an edge on the proximal end or the distal end of the patch.

23. The tape tab according to claim 22, wherein the support layer is continuous at least at the location where the at least one incision is cut through the patch.

24. The tape tab according to claim 22, wherein said at least one incision extends through an edge on the distal end of the patch.

25. The tape tab according to claim 22, wherein at least one of said incisions extends through an edge on the proximal end of the patch and at least one of said incisions extends through an edge on the distal end of the patch.

26. The tape tab according to claim 22, wherein said at least one incision extends through an edge on the proximal end of the patch.

27. A method of manufacturing an elongate strip, comprising the steps of:
providing an elongate strip of a male fastening means having two longitudinal edges along its length, said strip comprising a backing bearing a plurality of male fastening elements projecting from the backing surface, wherein the backing is not attached to a support layer, and
cutting a plurality of incisions in the strip such that none of the incisions extends through the width of the strip, thereby leaving the strip integral, wherein the incisions do not remove material from the strip.

28. A method of manufacturing an elongate strip, comprising the steps of:
providing an elongate strip of a male fastening means having two longitudinal edges along its length,
cutting a plurality of incisions in the strip such that none of the incisions extends through the width of the strip, thereby leaving the strip integral, wherein the incisions do not remove material from the strip, and
stretching the incised strip in a machine direction to form insections in the strip.

* * * * *